United States Patent [19]

Wernli et al.

[11] Patent Number: 4,558,116

[45] Date of Patent: Dec. 10, 1985

[54] PROCESS FOR PREPARING RELATIVELY HIGH MOLECULAR WEIGHT EPOXY RESINS

[75] Inventors: Walter L. Wernli, Angleton; Robert P. Shirtum, Freeport, both of Tex.

[73] Assignee: The Dow Chemical Company, Midland, Mich.

[21] Appl. No.: 707,976

[22] Filed: Mar. 4, 1985

[51] Int. Cl.$^4$ ............................................. C08G 59/06
[52] U.S. Cl. ...................................... 528/95; 525/507; 528/87; 549/517
[58] Field of Search ..................... 525/507; 528/87, 95, 528/104; 549/517

[56] References Cited

U.S. PATENT DOCUMENTS

| | | | |
|---|---|---|---|
| 2,848,435 | 8/1958 | Griffin et al. | 260/47 |
| 3,121,727 | 2/1964 | Baliker, Jr. et al. | 260/348.6 |
| 3,325,452 | 6/1967 | McWhorter et al. | 260/47 |
| 4,017,523 | 4/1977 | Vargiu et al. | 549/517 |
| 4,132,718 | 1/1979 | Vargiu et al. | 528/95 X |
| 4,373,073 | 2/1983 | Wojtech et al. | 549/517 X |

FOREIGN PATENT DOCUMENTS 1084332  9/1967  United Kingdom ................ 549/517

Primary Examiner—Earl Nielsen
Attorney, Agent, or Firm—J. G. Carter

[57] ABSTRACT

Epoxy resins low in aliphatic halogen are prepared by reacting a polyhydric phenol with an excess of an epihalohydrin in the presence of a secondary alcohol and an aqueous solution of an alkali metal hydroxide until from 45 to <70 percent of the phenolic hydroxyl groups have reacted; removing unreacted polyhydric phenol therefrom until less than 4% total phenolic hydroxyl remains in the reaction product; dehydrohalogenating the resultant intermediate product and recovering the epoxy resin therefrom.

18 Claims, No Drawings

PROCESS FOR PREPARING RELATIVELY HIGH MOLECULAR WEIGHT EPOXY RESINS

BACKGROUND OF THE INVENTION

The present invention pertains to the preparation of epoxy resins low in aliphatic halogen content.

Many applications of solid epoxy resins such as electrical laminates and encapsulations and the like require that the resins be low in halide content. The present invention provides a means for preparing epoxy resins low in halide content.

SUMMARY OF THE INVENTION

One aspect of the present invention pertains to an improvement in a process for preparing relatively low molecular weight epoxy resins by reacting at least one polyhydric phenol with an excess of at least one epihalohydrin in the presence of an alcohol and an aqueous solution of an alkali metal hydroxide followed by dehydrohalogenation of the resultant halohydrin intermediate wherein the improvement resides in (1) employing a secondary alcohol as the alcohol;

(2) terminating the reaction between the polyhydric phenol and the epihalohydrin when from about 40 to about <70, preferably from about 50 to about 60 percent of the phenolic hydroxyl groups have reacted thereby producing an intermediate reaction product;

(3) removing unreacted polyhydric phenol from the resultant intermediate reaction product such that the concentration of phenolic hydroxyl-containing material therein is less than about 4, preferably less than about 1 percent by weight;

(4) dehydrohalogenating the product from step (3) with a suitable dehydrohalogenating agent in a suitable inert solvent system; and (5) recovering from step (4) a glycidyl ether of a polyhydric phenol containing less than about 1500, preferably less than about 1000 ppm by weight aliphatic halogen.

Another aspect of the present invention pertains to an improvement in a process for preparing relatively high molecular weight epoxy resins by reacting a relatively low epoxy molecular weight epoxy resin with a polyhydric phenol in the presence of a catalytic quantity of a suitable catalyst wherein the improvement resides in employing as the relatively low equivalent weight epoxy resin, one which has been prepared by the aforementioned process.

DETAILED DESCRIPTION OF THE INVENTION

Suitable polyhydric phenols which can be employed herein include those represented by the formulas

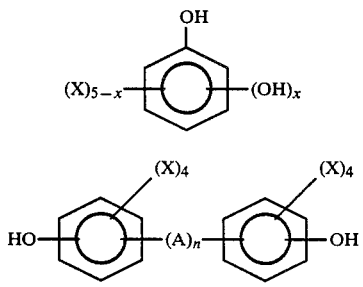

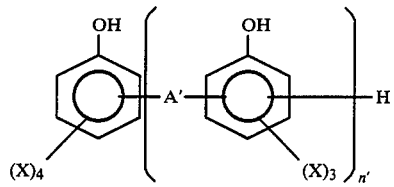

or

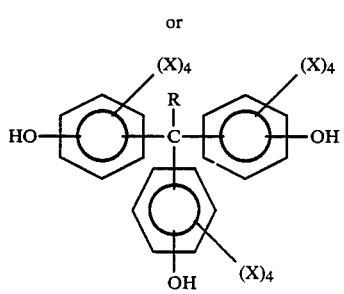

wherein A is a divalent hydrocarbon group having from 1 to about 12, preferably from 1 to about 6, carbon atoms,

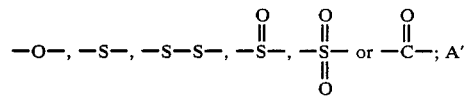

is a divalent hydrocarbon group having from 1 to about 12, preferably from 1 to about 6, carbon atoms; R is hydrogen or a hydrocarbyl group having from 1 to about 12, preferably from 1 to about 3 carbon atoms; each X is independently hydrogen or a hydrocarbyl group having from 1 to about 4, preferably from 1 to about 2, carbon atoms or a halogen, preferably chlorine or bromine; n has a value of zero or 1; n' has a value of from 1.001 to about 20, preferably from about 1.001 to about 12; and x has a value of 1 or 2.

Particularly suitable polyhydric phenols include, for example, bisphenol A (2,2-bis(4-hydroxyphenyl)propane), bisphenol F (bis(4-hydroxyphenyl)methane ) and trisphenol F (tris(4-hydroxyphenyl)methane), mixtures thereof and the like.

Suitable epihalohydrins which can be employed herein include, for example, those represented by the formula

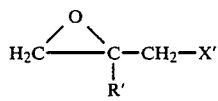

wherein R' is hydrogen or an alkyl group having from 1 to about 4 carbon atoms and X' is a halogen.

Particularly suitable epihalohydrins include, for example, epichlorohydrin, epibromohydrin, epiiodohydrin, methylepichlorohydrin, methylepibromohydrin, methylepiiodohydrin, mixtures thereof and the like.

Suitable catalysts which can be employed herein include, for example, alkali metal hydroxides such as, for example, sodium hydroxide, potassium hydroxide, mixtures thereof and the like.

Suitable secondary alcohols which can be employed herein include any such alcohol which has a solubility in water at 20° C. of greater than 20 percent by weight.

Particularly suitable secondary alcohols include, for example, isopropyl alcohol, 2-butanol, 2-hydroxypropyl methyl ether, 2-hydroxypropyl ethyl ether, mixtures thereof and the like.

Suitable dehydrohalogenating agents which can be employed herein include alkali metal hydroxides, alkali metal carbonates, mixtures thereof and the like.

The dehydrohalogenation reaction is conducted in the presence of an inert solvent or mixture of solvents in which the resin is soluble such as, for example, alcohols, ketones, glycol ethers, aromatic hydrocarbons, mixtures thereof and the like. Particularly suitable solvents include, for example, 2-butanol, 2-hydroxypropyl methyl ether, 2-hydroxypropyl ethyl ether and the like.

Suitable catalysts for effecting the reaction between the epoxy resin and the phenolic hydroxyl-containing compound include, for example, those disclosed in U.S. Pat. Nos. 3,306,872; 3,341,580; 3,379,684; 3,477,990; 3,547,881; 3,637,590; 3,843,605; 3,948,855; 3,956,237; 4,048,141; 4,093,650; 4,131,633; 4,132,706; 4,171,420; 4,177,216; 4,302,574; 4,320,222; 4,358,578; 4,366,295; and 4,389,520, all of which are incorporated herein by reference. It is, however, preferred not to employ a halogen containing catalyst since it will increase the halogen content.

Particularly suitable catalysts are those quaternary phosphonium and ammonium compounds such as, for example, ethyltriphenylphosphonium chloride, ethyltriphenylphosphonium acetate, ethyltriphenylphosphonium diacetate(ethyltriphenylphosphonium acetate.acetic acid complex), tetrabutylphosphonium acetate, tetrabutylphosphonium diacetate(tetrabutylphosphonium acetate·acetic acid complex), tetrabutylphosphonium tetrahaloborate, butyltriphenylphosphonium tetrabromobisphenate, butyltriphenylphosphonium bisphenate, butyltriphenylphosphonium bicarbonate, benzyltrimethylammonium chloride, benzyltrimethylammonium hydroxide, benzyltrimethylammonium tetrahaloborate, tetramethylammonium hydroxide, tetrabutylammonium hydroxide, and mixtures thereof and the like.

Other suitable catalysts include tertiary amines such as, for example, triethylamine, tripropylamine, tributylamine, 2-methylimidazole, benzyldimethylamine, mixtures thereof and the like.

In the coupling reaction, the alkali metal hydroxide is employed in amounts of from about 0.1 to about 0.6 moles of alkali metal hydroxide per phenolic hydroxyl equivalent and the epihalohydrin is employed in quantities of at least about 5 moles of epiphalohydrin per mole of phenolic-hydroxyl-containing material. The coupling reaction is conducted at a temperature of from about 10° to about 90° C., preferably from about 40° to about 60° C. The coupling reaction is conveniently stopped by neutralizing the alkali metal hydroxide such as, for example, with monosodium phosphate.

The dehydrohalogenation reaction is conducted at a temperature of from about 5° to about 90° C., preferably from about 30° to about 60° C. The dehydrohalogenation reaction is conducted, usually with repeated separation of the organic layer and new additions thereto of dehydrohalogenation agent, until the hydrolyzable halogen content is less than about 200.

The advancement reaction is usually conducted at a temperature of from about 120° to about 250° C., preferably from about 150° to about 200° C.

The epoxy resins of the present invention are suitable for such applications as laminates, composites, coatings, adhesives, castings, moldings, electronic encapsulations and in potting compositions.

Suitable solvents which can be employed in the preparation of coatings, laminates and the like include, for example, ketones, alcohols, glycol ethers and amides, such as, for example, acetone, methyl ethyl ketone, methanol, propylene glycol methyl ether and dimethyl formamide.

The products containing the epoxy resins of the present invention may also contain, if desired, pigments, dyes, mold release agents, flow control agents, reinforcing agents, fillers, fire retardant agents, rubber modifiers, surfactants, accelerators reactive diluents, mixtures thereof and the like.

The following examples are illustrative of the invention, but are not to be construed as to limiting the scope thereof in any manner.

EXAMPLE 1

A mixture of 456 grams of bisphenol A, 250 grams of epichlorohydrin, and 700 grams of isopropyl alcohol was reacted with 120 g of a 25% aqueous NaOH solution over a two-hour (7200s) period of time at 40° C. Approximately 50 percent of the phenolic hydroxyl groups remained unreacted.

Residual caustic in the reaction was neutralized using a dilute solution $NaH_2PO_4$, and water washed 3 times with 200 ml volumes of distilled water.

The non-resin components were distilled from the resin and the resin dissolved in methyl isobutyl ketone to obtain a solution containing 40 wt.% resin intermediates.

The bisphenol A and some resin intermediates were extracted from the solution using three 200 ml volumes of a 5% NaOH aqueous solution. The resulting resin intermediates contained 0.14 wt.% bisphenol A.

The mixture was reacted with an excess of an aqueous solution containing 16% NaOH and 9% $Na_2CO_3$ at 24° C. The organic and aqueous phases were repeatedly separated out and fresh caustic-carbonate solution added until the hydrolyzable chlorine content was 98 ppm.

The resin precursor was distilled to remove solvents and analyzed for aliphatic chlorine species. Total aliphatic chlorine content was 757 ppm, hydrolyzable chlorine was 98 ppm, ionic chlorine was 13 ppm and the resin contained 19.2% epoxide.

EXAMPLE 2

A mixture of 300 grams of p,p'-bisphenol A, 610 grams of epichlorohydrin and 410 grams of isopropyl alcohol was charged to a 2-liter glass reaction flask and heated to 40° C. The mixture was reacted using 21.25 grams of NaOH in a water solution. The NaOH solution was titrated in slowly over a one-hour period of time to achieve a 60% conversion of the hydroxyl groups of the bisphenol A. The mixture was allowed to react for an additional 2 hours (7200s) at 40° C. to deplete the remaining NaOH in the reaction flask. Approximately 62 percent of the phenolic hydroxyl groups had reacted.

The resulting reactants and products were allowed to cool to ambient temperature and the aqueous and organic phases separated. The organic components were neutralized with a dilute solution of $NaH_2PO_4$ and washed 3 times with 300 ml volumes of distilled water.

The organic solution was filtered, and the lower boiling components distilled from the resin intermediate.

The resin intermediates were dissolved in a solution of 70% methyl isobutyl ketone and 30% isopropyl alcohol, such that the resin intermediates were 40% by wt. of the total solution.

The organic solution was mixed with a 7% NaOH aqueous solution, 300 ml, for 3–5 minutes (150–180s) and the aqueous portion removed and stored. The above extraction was repeated 2 more times to extract as much of the phenolic hydroxyl containing species as was possible, about 0.4 percent unreacted bisphenol A remained in the resin intermediate.

The resin was epoxidized using a 5% excess of an aqueous solution of 16% NaOH and 9% $Na_2CO_3$, at 50° C. for 3 hours (10,800s). The epoxidation reaction was repeated until the resin chlorohydrin species were less than 200 ppm. The organic solution was neutralized using an $NaH_2PO_4$ solution and washed with distilled water until ionic chlorine was less than 1 ppm.

The solvents were distilled from the resin product and the resin was analyzed for total chlorine content. Total aliphatic chlorine content was 1385 ppm, including 188 ppm hydrolyzable chlorine.

The relatively low molecular weight epoxy resin prepared above was heated to 98° C. and bisphenol A was added in an amount calculated to achieve a final epoxide content of 8%. Two grams of a 70% solution of ethyltriphenylphosphonium acetate.acetic acid complex in methanol was added and the contents reacted at 185° C. for 2½ hours (9000s). The final epoxy resin contained 1030 ppm total aliphatic chlorine, 7.2% epoxide and 4 ppm ionic chlorine and hydrolyzable chlorine was 188 ppm.

EXAMPLE 3

A mixture of 456 grams of p,p'-bisphenol A, 925 grams of epichlorohydrin, and 400 grams of isopropyl alcohol was heated to 40° C. The mixture was reacted with 128 grams of 25% NaOH aqueous solution, titrated in over a one-hour (3600s) period of time and allowed to react a total of 2½ hours (9000s).

The mixture was allowed to react for an additional 2 hours (7200s) at 40° C. to deplete the remaining NaOH in the reaction flask. Approximately 62 percent of the phenolic hydroxyl groups had reacted.

The resulting reactants and products were allowed to cool to ambient temperature and the aqueous and organic phases separated. The organic components were neutralized with a dilute solution of $NaH_2PO_4$ and washed 3 times with 300 ml volumes of distilled water.

The organic solution was filtered, and the lower boiling components distilled from the resin intermediate.

The resin intermediates were dissolved in a solution of 70% methyl isobutyl ketone and 30% isopropyl alcohol, such that the resin intermediates were 40% by wt. of the total solution.

The organic solution was mixed with a 7% NaOH aqueous solution, 300 ml, for 3–5 minutes (150–180s) and the aqueous portion removed and stored. The above extraction was repeated 2 more times to extract as much of the phenolic hydroxyl containing species as was possible, about 0.6 percent unreacted bisphenol A remained in the resin intermediate.

The resin was epoxidized using a 5% excess of an aqueous solution of 16% NaOH and 9% $Na_2CO_3$, at 50° C. for 3 hours (10,800s). The epoxidation reaction was repeated until the resin chlorohydrin species were less than 200 ppm. The organic solution was neutralized using an $NaH_2PO_4$ solution and washed with distilled water until ionic chlorine was less than 1 ppm.

The resultant epoxy resin contained 328 ppm hydrolyzable chlorine, 3 ppm ionic chlorine, and a total aliphatic chlorine content of 1400 ppm.

The above prepared epoxy resin was mixed with a calculated amount of bisphenol A and a suitable catalyst, reacted at 185° C., to achieve a final resin containing 7.9% epoxide, 1020 ppm total aliphatic chlorine, and 311 ppm hydrolyzable chlorine.

EXAMPLE 4

A mixture of 456 grams of bisphenol A, 456 grams of epichlorohydrin and 700 grams of isopropyl alcohol was reacted with 127 grams of a solution containing 25% by weight NaOH and 75% $H_2O$, over a 2 hour (7200s) period of time at 40° C. The reaction was repeated 3 times to provide enough resin precursor material to perform the advancement reaction with bisphenol A.

The non-resin components were distilled from the resin and the resin was dissolved in methyl isobutyl ketone to obtain a solution containing 40 weight % resin intermediate.

The bisphenol A and resin intermediate containing a hydroxyl group were removed by repeated extractions, usually 3 to 5 extractions, using 200 ml volumes of 5% NaOH aqueous solution. The resulting residual resin intermediate contained 0.21% bisphenol A.

The resin intermediate in methyl isobutyl ketone solution was epoxidized using a 25% by weight solution of NaOH in $H_2O$, at 40° C., until the hydrolyzable chlorine content was less than 100 ppm. Several epoxidation reactions were performed to achieve the low hydrolyzable chlorine content. The organic solution was neutralized with an aqueous solution containing 10% $NaH_2PO_4$, and washed with several 200 ml batches of deionized water to remove the salt formed during epoxidation.

The resin precursor was vacuum stripped to remove the solvents and water and analyzed. The precursor contained 924 ppm total chlorine and 20.02% epoxide groups.

144.3 grams of resin precursor was heated to 150° C., 37.9 grams of bisphenol A was added and dissolved, and 950 ppm of ethyl triphenyl phosphonium acetate.acetic acid complex as a 70% by weight solution in dipropylene glycol was added as an advancement catalyst. The advancement reaction produced a resin containing 557 ppm total aliphatic chlorine content. The hydrolyzable chlorine content was 88 ppm.

EXAMPLE 5

A mixture of 456 grams of bisphenol A, 256 grams of epichlorohydrin, and 700 grams of isopropyl alcohol was reacted with 254 grams of a 25% NaOH aqueous solution for 2½ hours (9000s) at 40° C. 85% of the phenolic hydroxyl groups had reacted. The residual unreacted NaOH was neutralized using three 200 ml volumes of a 10% $NaH_2PO_4$ solution, the solution was then washed several times with 200 ml volumes of deionized water.

The volatile solvents were removed from the resin precursor by vacuum distillation, and the resin dissolved in methyl isobutyl ketone to 40% resin by weight.

The bisphenol A and resin intermediate containing hydroxyl groups were extracted using several volumes of a 5% NaOH aqueous solution until residual bisphenol A content was 0.17% by weight.

The resin precursor was epoxidized using a 25% by weight NaOH aqueous solution for 3 hours (10800s) at 40° C., and the residual NaOH neutralized using a 10% solution of NaH$_2$PO$_4$ in H$_2$O.

The residual organic solution was washed several times with 200 ml volumes of deionized water to remove salt (NaCl) produced during the epoxidation step.

Volatiles were vacuum stripped from the resin precursor, and the 641 grams of resin precursor analyzed at 13.7% epoxide content, 190 ppm hydrolyzable chlorine, and 1630 ppm total aliphatic chlorine.

The resin precursor was mixed with 77.0 grams of bisphenol A and 973 ppm of ethyl triphenyl phosphonium acetate.acetic acid complex catalyst and advanced to a solid epoxy resin containing 8.1% epoxide groups, and 1497 ppm total aliphatic chlorine.

COMPARATIVE EXPERIMENT

Example 5 was repeated, with the exception that no bisphenol A extraction was performed, and only 85% of the phenolic hydroxyl groups had reacted.

The resin precursor was epoxidized with 25% NaOH solution for 3 hours (10800s) at 40° C., but emulsions formed and were very difficult to break. The solution was neutralized using 10% NaH$_2$PO$_4$ solution and washed several times with 200 ml volumes of deionized water. The emulsion was removed during each water wash and discarded.

The residual organic solution was stripped of volatiles and produced a resin precursor containing 2640 ppm total chlorine, of which 471 ppm was hydrolyzable chlorine. The resin contained 13.5% epoxide groups.

The resin precursor (704 grams) was mixed with 79.0 grams of bisphenol A and 1.1 grams of ethyl triphenyl phosphonium acetate.acetic acid complex catalyst, and advanced to a solid epoxy resin containing 2200 ppm total aliphatic chlorine content.

We claim:

1. In a process for preparing relatively low molecular weight epoxy resins by reacting at least one polyhydric phenol with an excess of at least one epihalohydrin in the presence of an alcohol and an alkali metal hydroxide followed by dehydrohalogenation of the resultant halohydrin intermediate; the improvement which comprises
   (1) employing a secondary alcohol as the alcohol;
   (2) terminating the reaction between the polyhydric phenol and the epihalohydrin when from about 45 to less than about 70 percent of the phenolic hydroxyl groups have reacted and removing the unreacted epihalohydrin therefrom thereby producing a halohydrin intermediate product;
   (3) removing unreacted polyhydric phenol from the resultant halohydrin intermediate product such that the concentration of phenolic hydroxyl-containing material therein is less than about 4, preferably less than about 1 percent by weight;
   (4) dehydrohalogenating the product from step (3) with a suitable dehydrohalogenating agent; and
   (5) recovering from step (4) a glycidyl ether of a polyhydric phenol containing less than about 1500 ppm total aliphatic halogen by weight.

2. A process of claim 1 wherein
   (i) the reaction between the polyhydric phenol and the epihalohydrin is conducted at a temperature of from about 10° C. to about 90° C.;
   (ii) the reaction between the polyhydric phenol and the epihalohydrin is terminated when from about 50 to about 60% of the phenolic hydroxyl groups have reacted;
   (iii) a sufficient quantity of material containing unreacted polyhydric phenol is removed such that the quantity of phenolic hydroxyl-containing material is less than about 1 percent by weight;
   (iv) dehydrohalogenation is conducted at a temperature of from about 5° to about 90° C.

3. A process of claim 2 wherein
   (i) the reaction between the polyhydric phenol and the epihalohydrin is conducted at a temperature of from about 40° C. to about 60° C.;
   (ii) a sufficient quantity of material containing unreacted polyhydric phenol is removed such that the quantity of phenolic hydroxyl-containing material is less than about 1 percent by weight; and
   (iii) the dehydrohalogenation reaction is conducted at a temperature of from about 30° C. to about 60° C.

4. A process of claim 1 wherein said polyhydric phenol is bisphenol A, said epihalohydrin is epichlorohydrin, said alkali metal hydroxide is sodium hydroxide and said dehydrohalogenation agent is a mixture of sodium hydroxide and sodium carbonate.

5. A process of claim 2 wherein said polyhydric phenol is bisphenol A, said epihalohydrin is epichlorohydrin, said alkali metal hydroxide is sodium hydroxide and said dehydrohalogenation agent is a mixture of sodium hydroxide and sodium carbonate.

6. A process of claim 3 wherein said polyhydric phenol is bisphenol A, said epihalohydrin is epichlorohydrin, said alkali metal hydroxide is sodium hydroxide and said dehydrohalogenation agent is a mixture of sodium hydroxide and sodium carbonate.

7. In a process for preparing a relatively high molecular weight epoxy resin by reacting at least one relatively low molecular weight epoxy resin and at least one material containing about two phenolic hydroxyl groups per molecule in the presence of an effective quantity of a suitable catalyst for effecting the reaction between the relatively low molecular weight epoxy resin and the material containing about two phenolic hydroxyl groups per molecule; the improvement which comprises employing as the relatively low molecular weight epoxy resin, one which has been prepared by the process of claim 1.

8. A process of claim 7 wherein said material containing about two phenolic hydroxyl groups is bisphenol A.

9. In a process for preparing a relatively high molecular weight epoxy resin by reacting at least one relatively low molecular weight epoxy resin and at least one material containing about two phenolic hydroxyl groups per molecule in the presence of an effective quantity of a suitable catalyst for effecting the reaction between the relatively low molecular weight epoxy resin and the material containing about two phenolic hydroxyl groups per molecule; the improvement which comprises employing as the relatively low molecular weight epoxy resin, one which has been prepared by the process of claim 2.

10. A process of claim 9 wherein said material containing about two phenolic hydroxyl groups is bisphenol A.

11. In a process for preparing a relatively high molecular weight epoxy resin by reacting at least one relatively low molecular weight epoxy resin and at least one material containing about two phenolic hydroxyl groups per molecule in the presence of an effective quantity of a suitable catalyst for effecting the reaction between the relatively low molecular weight epoxy resin and the material containing about two phenolic hydroxyl groups per molecule; the improvement which comprises employing as the relatively low molecular weight epoxy resin, one which has been prepared by the process of claim 3.

12. A process of claim 11 wherein said material containing about two phenolic hydroxyl groups is bisphenol A.

13. In a process for preparing a relatively high molecular weight epoxy resin by reacting at least one relatively low molecular weight epoxy resin and at least one material containing about two phenolic hydroxyl groups per molecule in the presence of an effective quantity of a suitable catalyst for effecting the reaction between the relatively low molecular weight epoxy resin and the material containing about two phenolic hydroxyl groups per molecule; the improvement which comprises employing as the relatively low molecular weight epoxy resin, one which has been prepared by the process of claim 4.

14. A process of claim 13 wherein said material containing about two phenolic hydroxyl groups is bisphenol A.

15. In a process for preparing a relatively high molecular weight epoxy resin by reacting at least one relatively low molecular weight epoxy resin and at least one material containing about two phenolic hydroxyl groups per molecule in the presence of an effective quantity of a suitable catalyst for effecting the reaction between the relatively low molecular weight epoxy resin and the material containing about two phenolic hydroxyl groups per molecule; the improvement which comprises employing as the relatively low molecular weight epoxy resin, one which has been prepared by the process of claim 5.

16. A process of claim 15 wherein said material containing about two phenolic hydroxyl groups is bisphenol A.

17. In a process for preparing a relatively high molecular weight epoxy resin by reacting at least one relatively low molecular weight epoxy resin and at least one material containing about two phenolic hydroxyl groups per molecule in the presence of an effective quantity of a suitable catalyst for effecting the reaction between the relatively low molecular weight epoxy resin and the material containing about two phenolic hydroxyl groups per molecule; the improvement which comprises employing as the relatively low molecular weight epoxy resin, one which has been prepared by the process of claim 6.

18. A process of claim 17 wherein said material containing about two phenolic hydroxyl groups is bisphenol A.

* * * * *